(12) United States Patent
Hoppe et al.

(10) Patent No.: US 8,290,570 B2
(45) Date of Patent: Oct. 16, 2012

(54) SYSTEM FOR AD HOC TRACKING OF AN OBJECT

(75) Inventors: Harald Hoppe, Achern (DE); Jose Luis Moctezume de la Barrera, Freiburg (DE)

(73) Assignee: Stryker Leibinger GmbH & Co., KG, Freiburg (DE)

( * ) Notice: Subject to any disclaimer, the term of this patent is extended or adjusted under 35 U.S.C. 154(b) by 1900 days.

(21) Appl. No.: 10/939,225

(22) Filed: Sep. 10, 2004

(65) Prior Publication Data

US 2006/0058644 A1    Mar. 16, 2006

(51) Int. Cl.
*A61B 5/00* (2006.01)

(52) U.S. Cl. ........ 600/424; 600/429; 606/86 R; 606/130

(58) Field of Classification Search .................. 600/424, 600/429; 606/79, 86, 87, 88, 89, 130
See application file for complete search history.

(56) References Cited

U.S. PATENT DOCUMENTS

| | | | |
|---|---|---|---|
| 4,323,459 A | 4/1982 | Quinlan | 210/700 |
| 4,396,945 A | 8/1983 | DiMatteo et al. | 358/107 |
| 4,722,056 A | 1/1988 | Roberts et al. | 364/413 |
| 4,869,247 A | 9/1989 | Howard, III et al. | 128/303.1 |
| 4,923,459 A | 5/1990 | Nambu | 606/130 |
| 4,945,914 A | 8/1990 | Allen | 128/653 R |
| 4,951,653 A | 8/1990 | Fry et al. | 128/24 A |
| 4,991,579 A | 2/1991 | Allen | 128/653 R |
| 5,016,639 A | 5/1991 | Allen | 128/653 R |
| 5,094,241 A | 3/1992 | Allen | 128/653.1 |
| 5,097,839 A | 3/1992 | Allen | 128/653.1 |
| 5,119,817 A | 6/1992 | Allen | 128/653.1 |
| 5,142,930 A | 9/1992 | Allen et al. | 74/469 |
| 5,178,164 A | 1/1993 | Allen | 128/898 |
| 5,186,174 A | 2/1993 | Schlondorff et al. | 128/653.1 |
| 5,198,877 A | 3/1993 | Schulz | 356/375 |
| 5,211,164 A | 5/1993 | Allen | 128/653.1 |
| 5,222,499 A | 6/1993 | Allen et al. | 128/653.1 |
| 5,230,338 A | 7/1993 | Allen et al. | 128/653 |
| 5,309,101 A | 5/1994 | Kim et al. | 324/309 |
| 5,383,454 A | 1/1995 | Bucholz | 128/653.1 |
| 5,394,875 A | 3/1995 | Lewis et al. | 128/660.09 |
| 5,397,329 A | 3/1995 | Allen et al. | 606/73 |
| 5,494,034 A | 2/1996 | Schlondorff et al. | 128/653.1 |
| 5,515,160 A | 5/1996 | Schulz et al. | 356/241 |

(Continued)

FOREIGN PATENT DOCUMENTS

DE    3904595    14/1990

(Continued)

OTHER PUBLICATIONS

"Kinematik Approach to Hip Navigation," José Moctezuma Jul. 24, 2002 (4 pages).

(Continued)

*Primary Examiner* — Brian Casler
*Assistant Examiner* — Amanda Lauritzen
(74) *Attorney, Agent, or Firm* — McCracken & Frank LLC

(57) ABSTRACT

A method, system and device for tracking an anatomical structure includes a section having a small cross section relative to the length, a first end of the section having a tip capable of being removably attached to the anatomical structure; and a second end of the section that has two position-indicating sensors located thereon. The position-indicating sensors are tracked and displayed by the system.

59 Claims, 10 Drawing Sheets

U.S. PATENT DOCUMENTS

| | | | |
|---|---|---|---|
| 5,551,429 A | 9/1996 | Fitzpatrick et al. | 128/653.1 |
| 5,575,794 A | 11/1996 | Walus et al. | 606/116 |
| 5,590,215 A | 12/1996 | Allen | 382/128 |
| 5,595,193 A | 1/1997 | Walus et al. | 128/898 |
| 5,617,857 A | 4/1997 | Chader et al. | 128/653.1 |
| 5,622,170 A | 4/1997 | Schulz | 128/653.1 |
| 5,638,819 A | 6/1997 | Manwaring et al. | 128/653.1 |
| 5,665,090 A | 9/1997 | Rockwood et al. | 606/80 |
| 5,695,501 A | 12/1997 | Carol et al. | 606/130 |
| 5,704,897 A | 1/1998 | Truppe | 600/117 |
| 5,711,299 A | 1/1998 | Manwaring et al. | 128/653.1 |
| 5,730,130 A | 3/1998 | Fitzpatrick et al. | 128/653.1 |
| 5,752,513 A | 5/1998 | Acker et al. | 128/653.1 |
| RE35,816 E | 6/1998 | Schulz | 356/376 |
| 5,769,789 A | 6/1998 | Wang et al. | 600/414 |
| 5,797,924 A | 8/1998 | Schulte et al. | 606/130 |
| 5,799,099 A | 8/1998 | Wang et al. | 382/131 |
| 5,851,183 A | 12/1998 | Bucholz | 600/425 |
| 5,871,445 A | 2/1999 | Bucholz | 600/407 |
| 5,880,976 A | 3/1999 | DiGioia, III et al. | 703/7 |
| 5,891,034 A | 4/1999 | Bucholz | 600/426 |
| 5,891,157 A | 4/1999 | Day et al. | 606/130 |
| 5,907,395 A | 5/1999 | Schulz et al. | 356/139.03 |
| 5,916,164 A | 6/1999 | Fitzpatrick et al. | 600/426 |
| 5,921,992 A | 7/1999 | Costales et al. | 606/130 |
| 5,954,648 A | 9/1999 | Van Der Brug | 600/411 |
| 5,970,499 A | 10/1999 | Smith et al. | 707/104 |
| 5,987,349 A | 11/1999 | Schulz | 600/427 |
| 6,073,044 A | 6/2000 | Fitzpatrick et al. | 600/426 |
| 6,081,336 A | 6/2000 | Messner et al. | 356/375 |
| 6,112,113 A | 8/2000 | Van Der Brug et al. | 600/427 |
| 6,205,411 B1 | 3/2001 | DiGioia, III et al. | 703/11 |
| 6,409,686 B1* | 6/2002 | Guthrie et al. | 600/587 |
| 6,430,434 B1 | 8/2002 | Mittelstadt | 600/426 |
| 6,453,190 B1 | 9/2002 | Acker et al. | 600/424 |
| 6,676,706 B1 | 1/2004 | Mears et al. | 623/22.4 |
| 6,695,850 B2 | 2/2004 | Diaz | 606/91 |
| 6,711,431 B2 | 3/2004 | Sarin et al. | 600/426 |
| 8,012,107 B2* | 9/2011 | Einav et al. | 601/5 |
| 2001/0034530 A1 | 10/2001 | Malackowski et al. | 606/130 |
| 2003/0153829 A1 | 8/2003 | Sarin et al. | 600/426 |
| 2003/0187351 A1* | 10/2003 | Franck et al. | 600/429 |
| 2004/0034313 A1 | 2/2004 | Leitner | 600/595 |
| 2004/0097952 A1* | 5/2004 | Sarin et al. | 606/102 |
| 2005/0085715 A1* | 4/2005 | Dukesherer et al. | 600/424 |
| 2007/0016009 A1* | 1/2007 | Lakin et al. | 600/424 |
| 2010/0160771 A1* | 6/2010 | Gielen et al. | 600/424 |
| 2012/0004668 A1* | 1/2012 | Wallace et al. | 606/130 |

FOREIGN PATENT DOCUMENTS

| | | |
|---|---|---|
| EP | 0 326 768 | 8/1989 |
| EP | 1399707 | 3/2004 |
| EP | 1417941 | 5/2004 |
| JP | 3-267054 | 11/1991 |
| JP | 06-282889 | 10/1994 |
| JP | 06-282890 | 10/1994 |
| WO | WO 90/05494 | 5/1990 |
| WO | WO 00/39576 | 7/2000 |
| WO | WO 02/063236 | 8/2002 |
| WO | WO 03/073951 | 9/2003 |
| WO | WO 2004/014219 | 2/2004 |
| WO | WO 2004/030556 | 4/2004 |
| WO | WO 2004/030559 | 4/2004 |

OTHER PUBLICATIONS

"Surgical Steps for Computer Assisted Total Hip Arthroplasty," HipTrac V1.0 José Luis Moctezuma de la Barrera Jun. 4, 2000 (6 pages).
"Software Requirements Specification (SRS) Image Enhanced Knee Navigation, #1728," Richard Aschenbrenner Jun. 23, 2003 (46 pages).
"Rx90® Total Hip System Acetabular Series," Biomet Orthopedics, Inc. 2001 (11 pages).
"Radiographic and Non-Invasive Determination of the Hip Joint Center Location: Effect on Hip Joint Angles," R.N. Kirkwood et al. Oct. 16, 2003 (3 pages).
"Hip Joint Anatomy," http://vv.totaljoints.info/HIPJOINT_anatomydetails.htm Oct. 7, 2003 (3 pages).
"Virtual Planning of Hip Operations and Individual Adaption of Endoprostheses in Orthopaedic Surgery," H. Handels et al. (12 pages).
"Inclination," http://www.gentili.net/thr/inclinat.htm Oct. 16, 2003 (1 page).
"Hip: Functional Method," http://kwon3d.com/manuals/kwon3d30/modeling/hip_func.html Oct. 16, 2003 (4 pages).
Web page from http://www.totaljoints.info/NORMALHIPJOINTIMAGE.jpg Oct. 7, 2003 (1 page).
Web page from http://www.totaljoints.info/REPLACEDHIPJOINTIMAGE.jpg Oct. 7, 2003 (1 page).
Web page from http://www.totaljoints.info/ANT_approach2.jpg Oct. 7, 2003 (1 page).
Web page from http://www.totaljoints.info/POST_approach2.jpg Oct. 7, 2003 (1 page).
Birkfellner et al., "Evaluation and Detection of Systematic Distortions in DC-pulsed Electromagnetic Position Sensing Devices," *Elsevier Science B. V.*, 1998, pp. 927-928.
Birkfellner et al., "Systematic Distortions in Magnetic Position Digitizers," *Med. Phys.* 25 (11), pp. 2242-2248 (Nov. 1998).
Livingston et al., "Magnetic Tracker Calibration for Improved Augmented Reality Registration," *Presence*, vol. 6, No. 5, pp. 532-546 (Oct. 1997).
State et al., "Superior Augmented Reality Registration by Integrating Landmark Tracking and Magnetic Tracking," Proceedings of SIGGRAPH 96 (New Orleans, LA, Aug. 4-9, 1996). In *Computer Graphics* Proceedings, Annual Conference Series, pp. 429-438.
Birkfellner et al., "Calibration of Tracking Systems in a Surgical Environment," *IEEE Tansactions on Medical Imaging*, Nov. 17, 1998, pp. 1-6.
Birkfellner et al., "Evaluation of Magnetic Position Digitizers for Computer Assisted Surgery," *Comput. Aided Surg.* 2(3/4), 225 (1997).
International Search Report and Written Opinion dated Aug. 15, 2001, Int'l. Appl. No. PCT/US01/02166.
Applied Neurophysiology, Journal of Stereotactic and Functional Neurosurgery, Proceedings of the Meeting of the American Society for Stereotactic and Functional Neurosurgery, Montreal, Quebec, (Jun. 3-6, 1987) Jan. 1998.
Stereotactic & Functional Neurosurgery vol. 53, No. 3, (1989) pp. 197-201.
Journal of Ultrasound in Medicine vol. 9, No. 9, (Sep. 1990), pp. 525-532.
Ultrasound in Neurosurgery J.M. Rubin et al. ISBN: 0881675490, pp. 47-58.
Stereotactic & Functional Neurosurgery vol. 54-55, (1990), pp. 419, 422, 423, 471-476, 482-487, 488-492, 493-496, 497, 498, 500.
British Journal of Neurosurgery vol. 4, No. 3, (1990), pp. 193-197.
IEEE Computer Graphics & Applications vol. 3, No. 10, (May 1990), pp. 43-51.
Journal of Neurosurgery vol. 72, No. 2, (Feb. 1990), pp. 355a.
IEEE Engineering in Medicine & Biology Society—Proceedings of 11th Annual International Conference, (1989), pp. 925, 926-929.
British Journal of Neurosurgery vol. 3, No. 5, (1989), pp. 561-568, 569-574.
British Journal of Neurosurgery vol. 3, No. 3, (1989), pp. 327-331.
Acta Neurochirurgica Supplementum 46, (1989), pp. 112-114.
Journal of Neurosurgery vol. 65, No. 4, (Oct. 1986), pp. 550-554, 557-559.
Journal of Neurosurgery vol. 57, No. 2, (Aug. 1982), pp. 157-163.
Neurosurgery vol. 10, No. 5, (May 1982), pp. 580-586.
Neurosurgery vol. 10, (Mar. 1982), pp. 375-379.
Guided Brain Operations E.A. Spiegel ISBN: 3805534515, (1982), pp. 23, 25, 28.
American Journal of Neuroradiology vol. 2, No. 2 (Mar./Apr. 1981), pp. 181-184.
Neurosurgery vol. 8, No. 1 (Jan. 1981), pp. 72-82.
Surgical Neurology vol. 14, No. 6, (Dec. 1980), pp. 451-464.
Investigative Radiology vol. 15, No. 4, (Jul./Aug. 1980), pp. 308-312.
Applied Neurophysiology vol. 43, No. 3-5, (1980), pp. 170-171, 172-173, 174-175.
Neurosurgery vol. 3, No. 2, (Sep./Oct. 1978), pp. 157-161.

* cited by examiner

SYSTEM FOR AD HOC TRACKING OF AN OBJECT

BACKGROUND

1. Technical Field

This invention relates generally to small tracking devices for use with surgical navigation systems. More particularly, this invention relates to a positional device that assists in determining the position and relative movement of an anatomical structure within a patient in a relatively non-invasive manner.

2. Background Art

The use of surgical navigation systems for assisting surgeons during surgery is quite common. Some systems are used to track the movement of bony structures. Determining the precise location of a bony structure, and whether it has moved, is essential when utilizing computer assisted surgical instruments in fields such as orthopedic surgery. Typical surgical navigation systems utilize relatively large tracking devices that are rigidly attached to the underlying bony structure being monitored. Rigid attachment of navigation trackers to the bony structure is often an extremely invasive procedure that may cause additional trauma to the patient and wastes a significant amount of time. The use of relatively large tracking devices necessitates a more robust attachment device, including a larger barb or other device to attach the tracking device to the bone. In addition, the bicortical fixation of these large tracking devices can increase the risk of postoperative fracture or infection. The present invention provides small tracking devices that can be affixed to the bone in a less invasive manner to assist a surgical navigation system monitor the position and change in position of a bony structure.

SUMMARY OF THE INVENTION

One embodiment of the present invention is directed toward a system for determining a position of an anatomical structure that includes a surgical navigation system having a display and two tracking devices, the tracking devices each having a rigid section configured for insertion into a skeletal structure of a subject, the section including a first end and a second end, the section further having a small cross section relative to a length of the section. Further, the tracking device has a joint having a first and second degrees of freedom connected to the first end of the section, and a tip attached to the joint, where the tip includes means for being removably attached to the anatomical structure. Two position-indicating sensors that can be tracked by the surgical navigation system are disposed on the second end of the rigid section in a fixed relation to each other. A first circuit configured for calculating a global position of the skeletal structure by correlating positional information from the tracking devices; and a second circuit configured for displaying the global position of the anatomical structure on the display are also provided.

A further embodiment of the present invention is directed towards a system for determining a position of an anatomical structure that comprises a surgical navigation system having a display, a minimum of two tracking devices, the tracking devices each having a rigid section configured for insertion into a subject, the section including a first end and a second end, The section further has a small cross section relative to a length of the section. A joint having one or two degrees of freedom is connected to the first end of the section, In addition, the device includes a tip attached to the joint, wherein the tip comprises means for being removably attached to the skeletal structure, and two position-indicating sensors on the second end of the section in a fixed relation to each other, wherein the position-indicating sensors can be tracked by the surgical navigation system. The system also includes a first circuit configured for calculating a global position of the skeletal structure by correlating positional information from the tracking devices; and a second circuit configured for displaying the global position of the anatomical structure on the display.

An additional embodiment of the present invention is directed towards a system for determining a position of a skeletal structure that comprises a surgical navigation system having a display, and a tracking device having a rigid section configured for insertion into a subject, the section including a first end and a second end, the section further having a small cross section relative to a length of the section. The tracking device also includes a joint having first and second degrees of freedom connected to the first end of the section, a tip attached to the joint, wherein the tip comprises means for being removably attached to the skeletal structure, and at least three position-indicating sensors on the second end of the section in a fixed relation to each other, wherein the position-indicating sensors can be tracked by the surgical navigation system. A fourth sensor is associated with the joint and configured to provide the surgical navigation system with a relative position of the tip relative to the position-indicatinng sensors. The system further includes a first circuit configured for calculating a global position of the skeletal structure by correlating positional information from the position indicating sensors and the fourth sensor; and a second circuit for displaying the global position of the anatomical structure on the display.

Another embodiment of the present invention relates to a system for determining a position of an anatomical structure that has a surgical navigation system having a display, a tracking device having a flexible section configured for insertion into a subject, the section including a first end and a second end, the section further having a small cross section relative to a length of the section. The device for use with the system further includes a tip disposed on the first end of the section, wherein the tip comprises means for being removably attached to the skeletal structure, three position-indicating sensors disposed on the second end of the section, wherein the sensors can be tracked by the surgical navigation system, and a fourth sensor associated with the flexible section to provide the surgical navigation system with a relative position of the tip and the three position-indicating sensors. The system also has a transceiver associated with the tracking device that is configured for two-way communication with the surgical navigation system. The system further includes a first circuit configured for calculating a global position of the skeletal structure by correlating positional information from the tracking device and relative positional information from the sensor; and a second circuit configured for displaying the global position of the anatomical structure on the display.

A further embodiment of the present invention is directed toward a system for determining a position of an anatomical structure that has a surgical navigation system having a display, and a minimum of two tracking devices. At least one of the two tracking devices has a rigid section configured for insertion into a body, the section including a first end and a second end, the section further having a small cross section relative to a length of the section and a tip on the first end of the section, wherein the tip comprises means for being removably attached to the anatomical structure. The device also includes a transceiver associated with the tracking device that is in two-way communication with the surgical navigation system, and a position-indicating sensor on the second end of the section, wherein the position-indicating sensor can be tracked by the surgical navigation system. The system also has a first circuit for calculating a global position of the anatomical structure by correlating positional information from the two tracking devices; and a second circuit for displaying the global position of the anatomical structure on the display.

Other aspects and advantages of the present invention will become apparent upon consideration of the following detailed description.

BRIEF DESCRIPTION OF THE DRAWINGS

FIG. 4b is a cross sectional view taken along the line 4b-4b in FIG. 4a;

DESCRIPTION OF THE PREFERRED EMBODIMENT(S)

Figure 1:
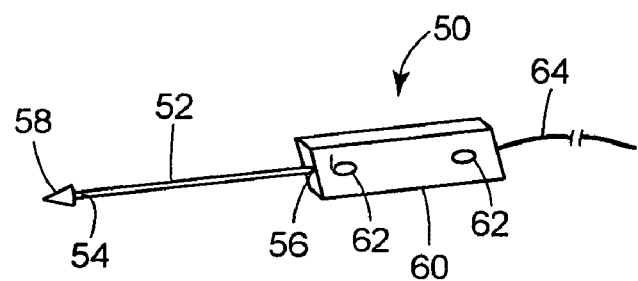
FIG. 1 is an isometric view of one embodiment of the present invention.
Figure 2:
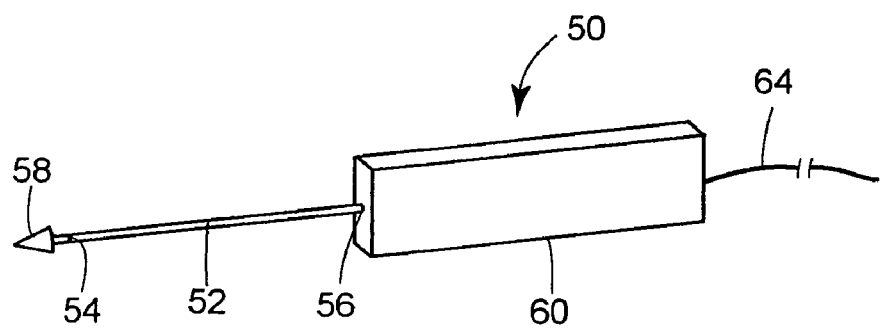
FIG. 2 is an isometric view of the opposite side of the embodiment of FIG. 1.

With reference to FIGS. 1 and 2, the present invention is directed toward a small tracking device 50 that includes a section 52 having a distal end 54 and a proximal end 56. A tip 58 is located at the distal end 54 of the section 52 and a body 60 is located at the proximal end 56 of the section 52. The section 52 can be either rigid or flexible and can be made from any surgically acceptable material including surgical stainless steel, fiber optic glass fibers and the like. The proximal end 56 of the section 52 is attached to the body 60. Mounted on the body 60 are two position-indicating devices 62. Examples of suitable position-indicating devices 62 include light emitting diodes (LEDs), reflective surfaces, acoustic devices and the like. These position-indicating devices 62 are well known and will not be described further. A preferred position-indicating device 62 is an LED that emits light in the infrared spectrum. Typically, the position-indicating devices 62 will be in a fixed relationship to each other. In one preferred embodiment of the present invention, the section 52 is rigid and the distance from the tip 58 to the position-indicating devices 62 is known.

The body 60 has an electrical conductor 64 attached to the internal leads of the position-indicating devices 62. The electrical conductor 64 provides power to the position-indicating devices 62 and for active position-indicating devices such as LEDs also provides a signal when each position-indicating-device 62 is to illuminate. Preferably, the body 60 and the position-indicating devices 62 are constructed from materials that can be sterilized at least one time. If the tracking device 50 is to be reusable, then the materials chosen for the tracking device 50 must be capable of repeated sterilization. Alternatively, the tracking device 50 can be formed from a surgically acceptable plastic that can be prepackaged in a sterile state and is discarded after a single use. The body 60 should be relatively small and lightweight. The body 60 can be made from the same materials as the section 52 or from different surgically acceptable materials. Preferably the materials used for the body 60 are lightweight so that the section 52 can be as thin as possible and if the section 52 is rigid, the weight of the body 60 will not cause the rigid section 52 to flex in use.

As indicated above, the cross section of the section 52 is small relative to the length of the section 52. The length of the section 52 need only be long enough so that the tip 58 can be attached to the bone or other anatomical structure and the body 60 is located outside the skin of the patient. Depending on the anatomy where the tracking device is to be used, the length of the section 52 from the tip 58 to the body 60 can be from about 1.5 to about 3.5 cm. The small nature of the cross section of the section 52 is very important so that the intrusion into the body of the patient is minimized. The section 52 needs to be thick enough so that if the section 52 is rigid and does not include a joint as discussed below, there will be no relative movement between the tip 58 and the body 60. For typical materials used in the formation of the section 52, the cross section can be any shape, but typically will be circular and preferably have a dimension of between about 1.5 and about 3.5 mm. The most preferred dimension for the cross section of the section 52 is between about 1.5 mm and about 2.5 mm.

FIG. 1 shows the tracking device 50 with two position-indicating devices 62 located collinear with the axis of the section 52. It is possible, as will be discussed later, to include more than two position-indicating devices 62 on the tracking device 50 and these position-indicating devices 62 can be arranged in any suitable arrangement, including being arranged in locations not collinear with the axis of the section 52, so long as the relationship among the position-indicating devices 62 is known. The distance between the position-indicating devices 62 on the body 60 need not be great. In fact, the position-indicating devices 62 can be located 2 mm from each other. The only requirement of the spacing of the position-indicating devices 62 is that the system can distinguish the emissions from each position-indicating device 62 from the next position indicating device 62. It is also possible to use a single position-indicating device 62 so long as a sufficient number of tracking devices 50 are attached to the anatomical structure.

Figure 3:
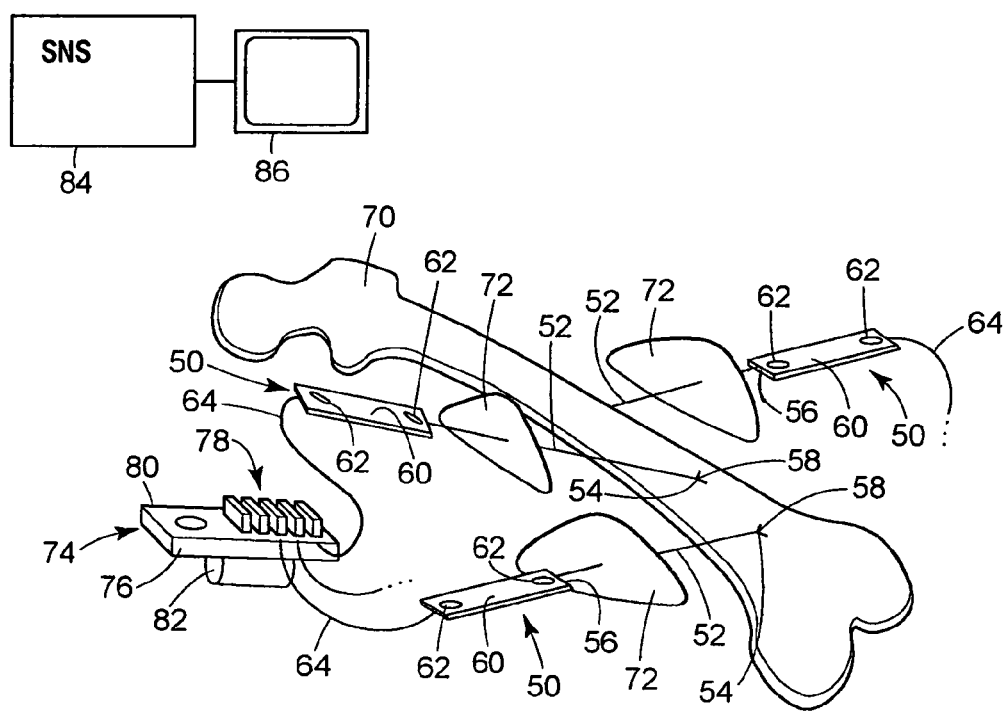
FIG. 3 is a schematic view of a system of the present invention showing the embodiment of FIG. 1 attached to a bone.

FIG. 3 shows the attachment of multiple tracking devices 50 to a bone 70 surrounded by tissue and skin 72, represented by the three patches of skin 72 as shown in FIG. 3. Each tracking device 50 is anchored to the bone 70. The minimum number of tracking devices 50 attached to the bone 70 to adequately track the location and orientation of the bone 70 depends on the exact configuration of the tracking device 50. As will be discussed in greater detail below, each tracking device can have one, two, three, or more position indicating devices 62. Further the number of tracking devices 50 necessary to adequately track the location and orientation of the bone 70 can also vary. Often more than the minimum number of tracking devices 50 will be used so that the system will constantly be able to see the minimum number of position-indicating devices 62 as the surgeon manipulates the anatomy or as the surgeon temporarily will block the field of view of the system.

A communication device 74 having a body 76 and a series of quick connect connectors 78 are attached to the electrical conductors 64. The communications device 74 has a transceiver 80 (represented by the transceiver window as shown) and a battery 82. The communications device 74 communicates in a wireless manner to a conventional surgical navigation system 84 that can track the position-indicating devices 62. The surgical navigation system is one well known in the art such as the system disclosed in U.S. Patent Publication No. 2001/034530, the disclosure of which is hereby incorporated by reference. It is also possible that the communication device 74 communicates with the surgical navigation system 84 using a hard-wired connection (not shown). The surgical navigation system 84 includes a display device 86, such as a computer monitor, to display the location of the various tracked devices 50. As the bone 70 is manipulated during a surgical procedure, the tracking devices 50 move with the bone and the position and orientation of the bone 70 can be tracked by the surgical navigation system 84 and displayed on the display device 86.

Figure 4:
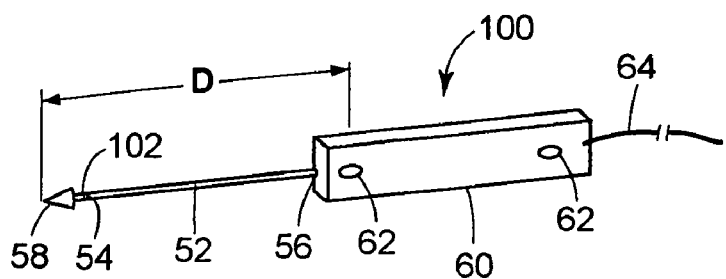
FIG. 4 is an isometric view of a further embodiment of the present invention.
Figure 4A:
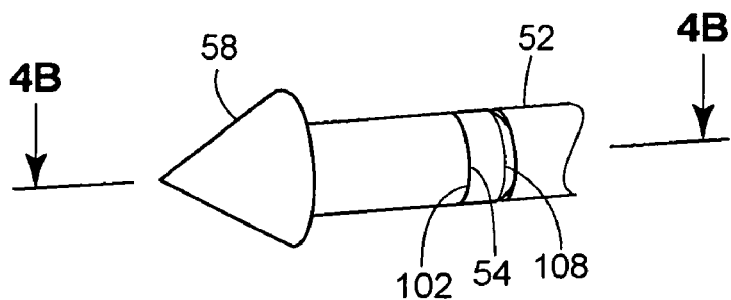
FIG. 4a is detailed view of the tip of the embodiment of FIG. 4.
Figure 4B:
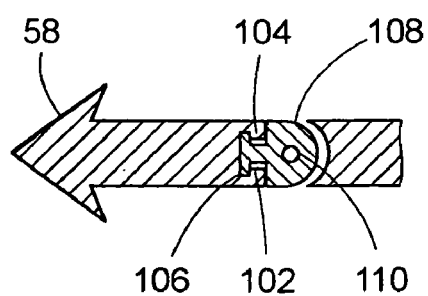

FIG. 4 shows an alternative embodiment of a tracking device 100 of the present invention. The tracking device 100 has the body 60, position-indicating devices 62, and the section 52, all similar to the device shown in FIG. 1. The tip 58 is attached to the distal end 54 of the section 52 by a coupling 102. The details of the coupling 102 are shown in FIGS. 4a and 4b. The coupling 102 has a rotating joint 104 that includes an undercut 106 that allows the distal end 54 and the tip 58 to freely rotate relative to each other. The rotating joint 104 is connected to a pivot joint 108 that includes a pivot pin 110. The pivot joint 108 allows the tip 58 to pivot relative to the section 52 of the device 100. Any suitable universal joint can be used in place of the rotating joint 104 and the pivot joint 108 so long as the distal end 54 can pivot relative to the section 58 in all directions. The device 100 can rotate in three dimensions relative to the tip 58. This is also referred to as having two degrees of freedom. The position-indicating devices 62 are located collinearly with the axis of the section 52. This enables the user to rotate the tracking device 100 so that the position-indicating devices 62 are always visible to the surgical navigation system 84. Because the relation between the joint 56 and the position-indicating devices 62 is known as indicated by the distance D, the tracking device 100 can be rotated and need not be recalibrated before the tracking device 100 can be properly tracked by the surgical navigation system 84. For the tracking device 100, at least three tracking devices 100 are needed to fully track the underlying anatomy.

Figure 5:
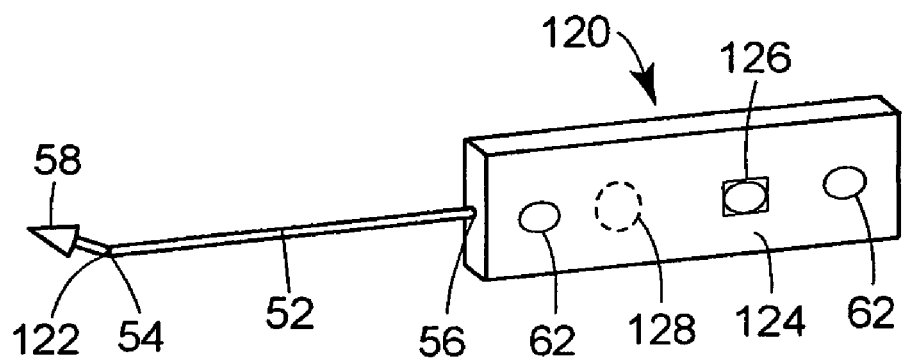
FIG. 5 is an isometric view of a still further embodiment of the present invention.
Figure 6:
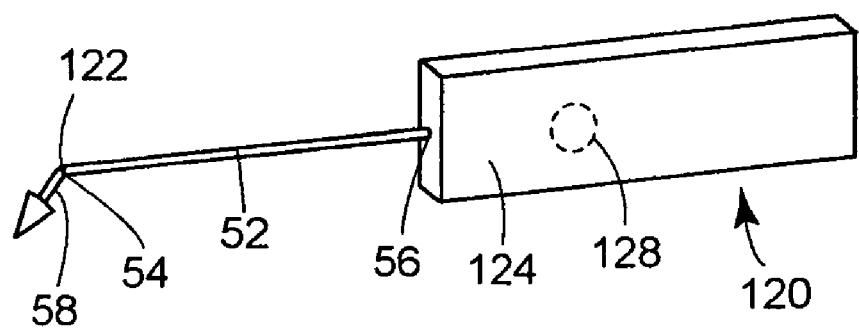
FIG. 6 is an isometric view of the opposite side of the embodiment of FIG. 5.

FIGS. 5 and 6 show a further embodiment of a tracking device 120. The tracking device 120 is similar to tracking device 50. The tip 58 is joined to the section 52 by a hinge joint 122 that is capable of hinging as shown. The hinge joint 122 has a single degree of freedom. This enables the tracking device 120 to easily be positioned for maximum visibility and also enables the tracking device to be calibrated in position as will be discussed below. The tracking device 120 has a body 124 that includes multiple position-indicating devices 62. In addition, the body 124 also includes a transceiver window 126 that covers a transceiver device capable of communication with a similar device in the surgical navigation system 84 in the same manner as the transceiver 80 as shown in FIG. 3. In addition, the tracking device 120 also includes its own self contained power supply 128, located within the body 124 and therefore shown in phantom, to power the transceiver 126 and the position-indicating devices 62. For tracking device 120, a minimum of at least two tracking devices 120 are needed to properly track the underlying anatomical structure.

Figure 7:
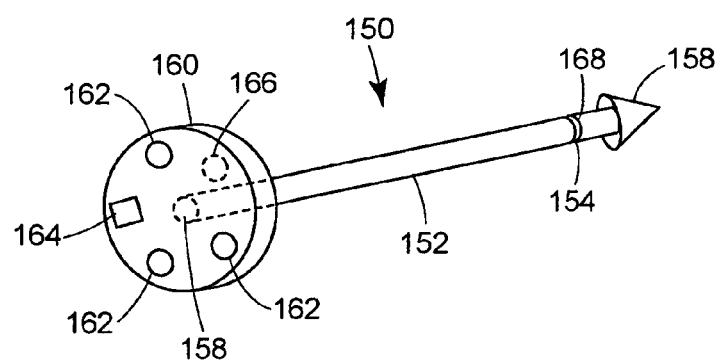
FIG. 7 is an isometric view of yet another embodiment of the present invention.

FIG. 7 shows a further embodiment of a tracking device 150 of the present invention. In this embodiment, the tracking device 150 includes a section 152 having a distal end 154 and a proximal end 156. The proximal end 156 is attached to a body 160 that is attached such that the body 160 is perpendicular to the axis of the section 152. The body 152 includes multiple position-indicating devices 162, three such devices are shown, and a transceiver 164. Internal to the body 160 is a battery 166, shown in phantom. The distal end 154 has a tip 158 attached by a joint 168. The joint 168 can be either the joint as shown in FIG. 4 or the hinging joint as shown in FIG. 5. In addition, the joint 168 can be eliminated and the section 152 can be rigid from the proximal end 156 to the tip 158.

Figure 8:
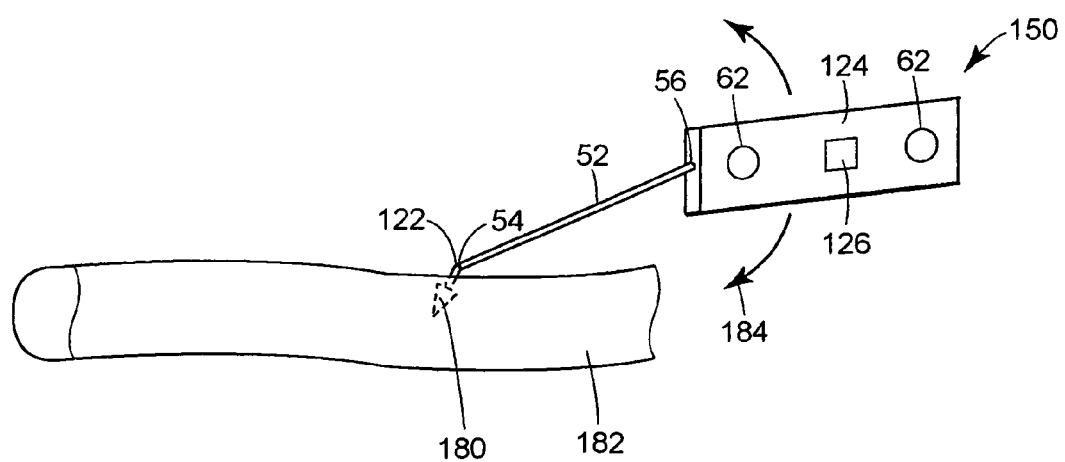
FIG. 8 is a schematic view showing the device of FIG. 5 attached to a bone and being rotated to determine the length of the section.

FIG. 8 shows the tracking device 150 attached at a point 180 to a bone 182. The tracking device 150 can be rotated about the point 180 as indicated by the arrows 184. This is a known method of calibrating a tracking device such as tracking device 150 in the field. The position-indicating devices 62 travel in an arc that forms a cone. The surgical navigation system 84 can track the position-indicating devices 62 and can then calculate the position 180 of attachment of the tracking device 150 to the bone 182. Because of the sensitivity of the surgical navigation system 84, only a small arc is needed to determine the length of the section 52. Therefore, the joint 122 is preferably located just above the cortex of the bone 182 and also below the skin of the patient. There will be sufficient motion to enable the surgical navigation system to locate the position of the joint 122 relative to the position-indicating devices 62.

Figure 9:
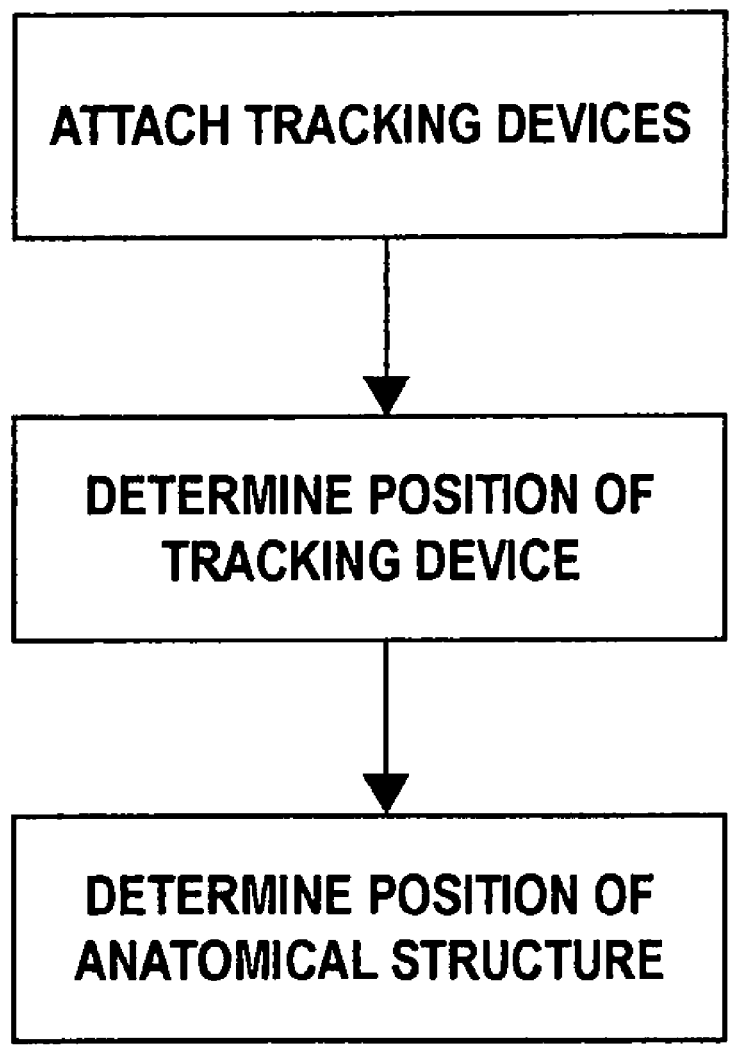
FIG. 9 is an block diagram of one embodiment of the method of the present invention.

FIG. 9 is a block diagram of the method steps of the present invention. At least two tracking devices such as the tracking device 50 are attached to a bone as indicated in the first step. The surgical navigation system 84 then determines the location of the tracking devices by locating the position-indicating devices 62. From the location of the tracking devices, the surgical navigation system 84 can determine the position of the anatomical structure, usually a bone. Typically, the surgical navigation system will display the position of the structure on the display 86.

Figure 10:
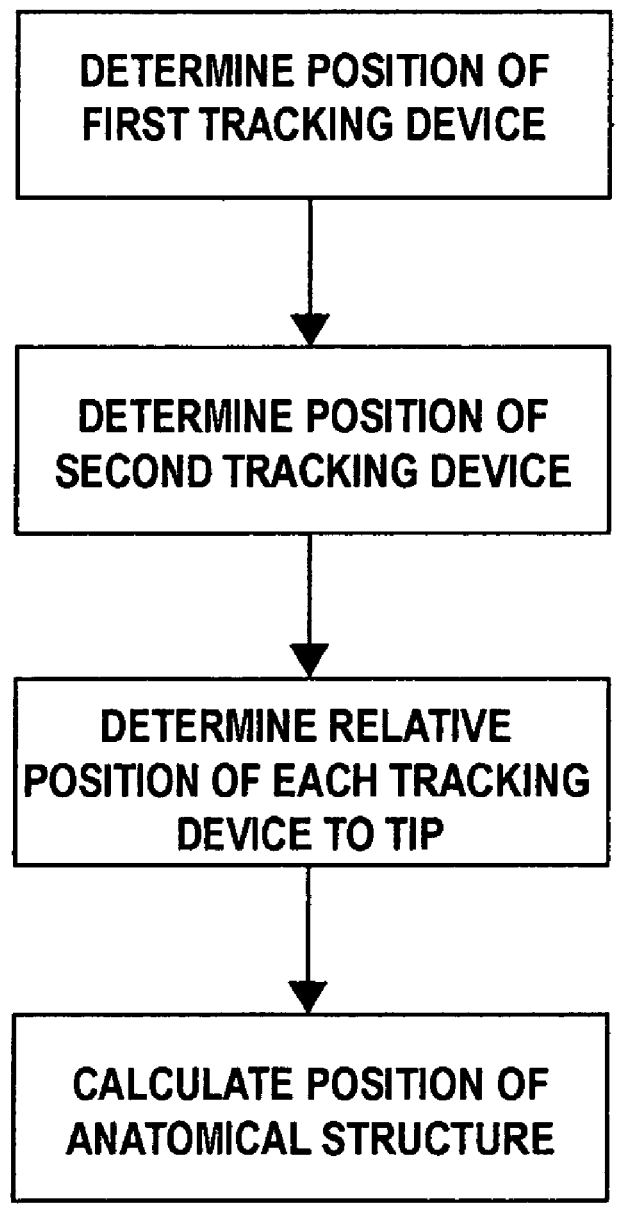
FIG. 10 is a block diagram of a further embodiment of the method of the present invention.

FIG. 10 shows a further block diagram of an alternative method of the present invention. In this embodiment, the position of a first tracking device is determined as has been described previously relative to the various tracking devices. Thereafter, the position of a second tracking device is also determined in a similar manner. Next, the position of the tracking device relative to the point of attachment to the anatomical structure is determined. This position is determined either based on the relative location of the tip 58 and the position-indicating devices 62 for fixed or rigid systems or as described below for non-rigid systems. Lastly, the position and orientation of the anatomical structure is determined. The determination is done using methods well known to those of skill in the art of computer assisted surgical navigation systems.

Figure 11:
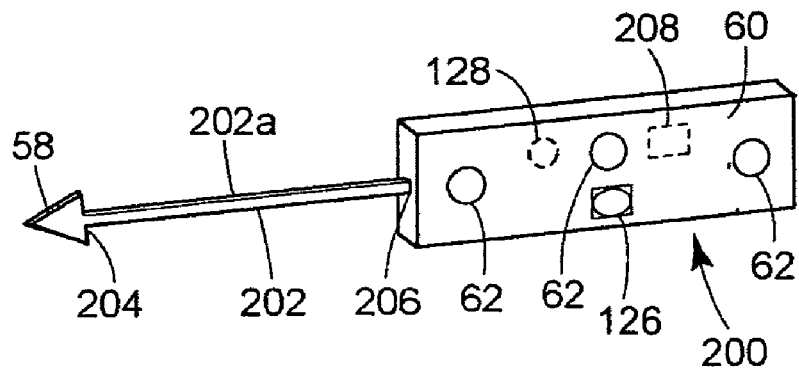
FIG. 11 is an isometric view of yet another embodiment of the present invention.

FIG. 11 shows a still added embodiment of a tracking device 200. The tracking device 200 has a flexible section 202 having a distal end 204 and a proximal end 206. The flexible section 202 can be a pair of fiber optic filaments 202a. The body 60 is attached to the proximal end 206 and includes position-indicating devices 62, the battery 128, the transceiver 126 and a fiber optic decoding device 208. The fiber optic deciding device 208 can determined the relative location of the tip 58 relative to the body 60 based on the amount of light that is returned by the return fiber optic element of the fiber optic pair 202a. This relative position of the tip 58 to the body 60 can be transmitted to the surgical navigation system 84 by the transceiver 126. Co-pending application Ser. No. 10/798,614, filed Mar. 11, 2004, has more detail on the functioning of the fiber optic pair to determine relative location and the disclosure of this application is hereby incorporated by reference. Other similar devices can be used such as strain gauges and the like. In addition, sensors built into the joint itself can determine the relative position. In this case, the relative position of the joint can be determined by electrical resistance changes, capacitance changes, magnetic sensors, and the like. The tracking device 200 can properly define the location of the underlying anatomy with a single tracking device 200.

Figure 12:
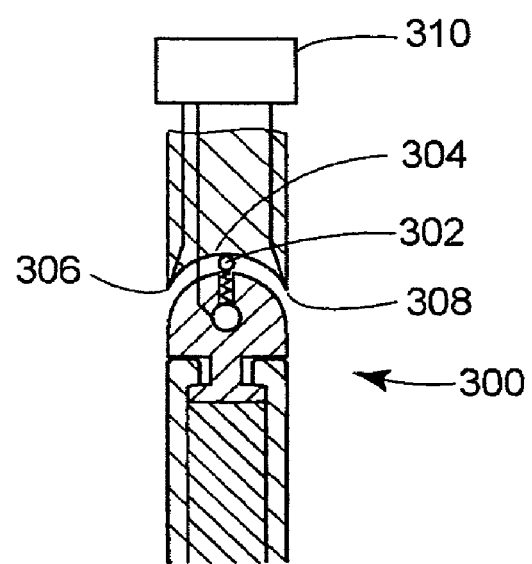
FIG. 12 is a schematic view of the coupling of FIG. 4 showing the use of a position encoder.

FIG. 12 shows an electric resistance encoder arrangement in a joint 300. A ball 302 contacts a resistive surface 304 that is electrically connected at ends 306 and 308 to an encoder device 310. The ball 302 is spring loaded to assure contact with the resistive surface 304 and the ball is also electrically connected to the encoder 310. Based on the relative resistance between the ends 306 and 308 of the resistive surface 304 and the ball 302, the encoder 310 can determine the relative position of the joint 300.

Figure 13:
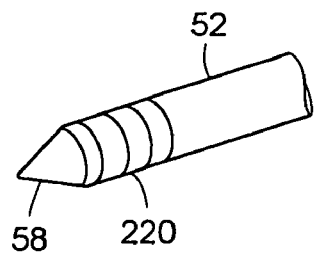
FIG. 13 is a detail view of an alternate tip of the embodiment of FIG. 1.

FIG. 13 shows an alternative embodiment of the tip 58. The tip 58 can either be a barb as shown in the prior figures or can be a screw device 220 as shown. In addition other methods of affixing the section 52 to the bone can also be used, such as surgical nails, adhesives and the like.

Figure 14:
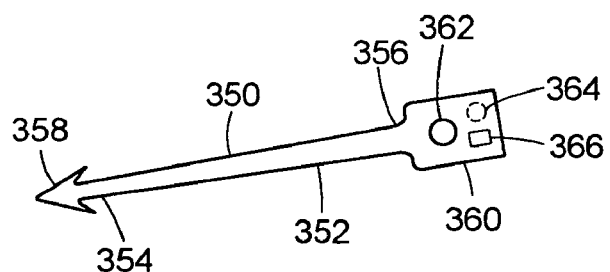
FIG. 14 is an isometric view of a still further embodiment of the present invention.

FIG. 14 depicts a tracking device 350 that has a section 352, a distal end 354 of the section 352 and a proximal end 356 of the section 352. The distal end 354 includes an integrally formed tip 358 and the proximal end 356 includes an integrally formed body area 360. The body area 360 includes a single position indicating device 362, a battery 364 (shown in phantom) contained within the body area 360 and a transceiver 366 to communicate with the surgical navigation system 84. The tip 358, the section 352 and the body area 360 are all formed from the same material. The tracking device 350 can be formed from materials that can be pre-sterilized for single use. A minimum of three of the tracking devices 350 are needed to define a location of the underlying anatomy for the surgical navigation system 84.

Figure 15:
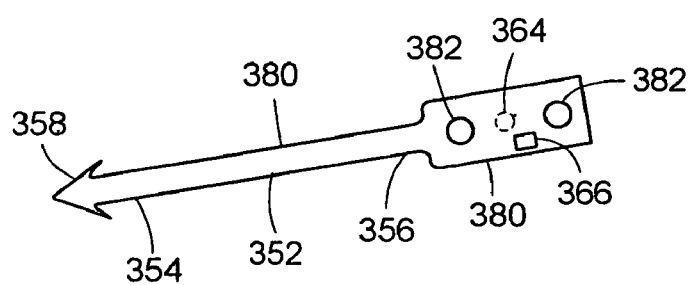
FIG. 15 is an isometric view of a yet additional embodiment of the present invention.

FIG. 15 shows a tracking device 380 that is similar to the device 350 shown in FIG. 14. The tracking device 380 has a body area 382 that is integral with the section 352 and the body area 382 includes two position-indicating devices 384.

Figure 16:
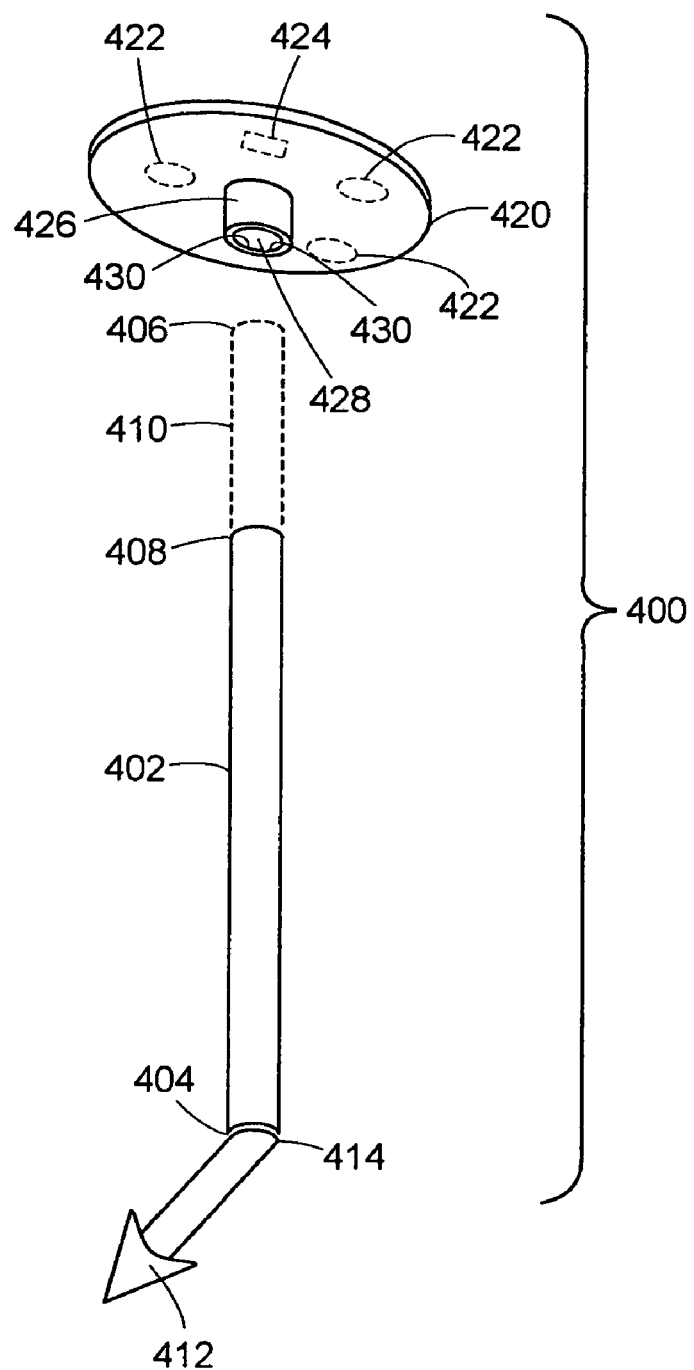
FIG. 16 is an exploded isometric view of another embodiment of the present invention.

In addition to the calibration method described relative to FIG. 8, other methods of determining the length of the section 152 can be used. These include an optical sensing device that can read optical coding located on the section 152; a resistive circuit that determines the length of the section 152 based on the electric resistance to a known voltage; or by directly digitizing the proximal end 156 using a known tracked pointing device. As shown in FIG. 16, a tracking device 400 has a separate section 402. The section 402 has a distal end 404 and a proximal end 406. In use, the section 402 is cut at a point 408 to remove a portion 410 of the section 402. Typically the section 402 is shortened to a length just above the skin of the patient to minimize interference with the surgical site and to maximize ergonomics. The distal end 404 is connected to a tip 412 by a joint 414 similar to those discussed previously. The tracking device 400 also has a separate body 420 that includes on its top surface a series of tracking sensors 422 and a transceiver window 424 (both shown in phantom). The body 420 also has a coupling 426 that has an opening 428. The inside wall of the coupling 426 also has a series of flexible bayonet structures 430 spaced around the interior of the coupling 426. These bayonet structures 430 will engage the section 402 as it is inserted into the coupling 426 and hold the section 402 firmly in place. In addition, the cross section of the section 402 and the opening 428 should match and they may be a shape other than circular to minimize relative movement of the body 420 and the section 402.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved

We claim:

1. A system for determining a position of an anatomical structure, comprising:
    a surgical navigation system having a display;
    two tracking devices wherein each tracking device comprises:
    a rigid section configured for insertion into a skeletal structure of a subject, the section including a first end and a second end, the section further having a small cross section relative to a length of the section,
    a joint having first and second degrees of freedom connected to the first end of the section,
    a tip attached to the joint, wherein the tip includes means for being removably attached to the skeletal structure, and
    two position-indicating sensors on the second end of the section in a fixed relation to each other, wherein the position-indicating sensors can be tracked by the surgical navigation system;
    wherein the surgical navigation system further comprises a first circuit configured for calculating a global position of the skeletal structure by correlating positional information from the tracking devices, and a second circuit configured for displaying the global position of the skeletal structure on the display.

2. The system of claim 1 that includes a body at the second end of the section and the two position-indicating sensors are located on the body.

3. The system of claim 2, wherein the body is integral with the section.

4. The system of claim 2, wherein the body is perpendicular to an axis of the section.

5. The system of claim 1, wherein the position-indicating sensors are located co-linear with the axis of the section.

6. The system of claim 1, wherein the position-indicating sensors are located a known distance from the joint.

7. The system of claim 1, wherein the position-indicating sensors comprise an optical tracking element.

8. The system of claim 7, wherein the optical tracking element includes a LED.

9. The system of claim 1 that includes a transceiver associated with at least one said tracking device that is in two-way communication with the surgical navigation system.

10. The system of claim 9, wherein the transceiver is integrally formed with the tracking device.

11. The system of claim 1, wherein an external power supply provides energy to the tracking device through a wire.

12. The system of claim 1, wherein an internal battery provides energy to the tracking device.

13. A system for determining a position of an anatomical structure, comprising:
   a surgical navigation system having a display;
   a minimum of two tracking devices, wherein each said tracking device further comprises:
      a rigid section configured for insertion into a subject, the section including a first end and a second end, the section further having a small cross section relative to a length of the section,
      a joint having one or two degrees of freedom connected to the first end of the section,
      a tip attached to the joint, wherein the tip comprises means for being removably attached to a skeletal structure, and
      two position-indicating sensors on the second end of the section in a fixed relation to each other, wherein the position-indicating sensors can be tracked by the surgical navigation system;
   a first circuit configured for calculating a global position of the skeletal structure by correlating positional information from the tracking devices; and
   a second circuit configured for displaying the global position of the skeletal structure on the display.

14. The system of claim 13 that includes a body at the second end of the section and the two position-indicating sensors are located on the body.

15. The system of claim 14, wherein the body is integral with the section.

16. The system of claim 14, wherein the body is perpendicular to an axis of the section.

17. The system of claim 13, wherein the joint is configured for rotation in all directions.

18. The system of claim 13, wherein a position sensing unit provides information on the relative position of the first end of the section and the two position-indicating sensors.

19. The system of claim 13, wherein the position-indicating sensors are located co-linear with the axis of the section.

20. The system of claim 13, wherein the position-indicating sensors are located at a fixed distance from the joint.

21. The system of claim 13, wherein the position-indicating sensors comprise an optical tracking element.

22. The system of claim 21, wherein the optical tracking element includes a LED.

23. The system of claim 13, wherein an external power supply provides energy to the tracking devices through a wire.

24. The system of claim 13, wherein an internal battery provides energy to each of the tracking devices.

25. The system of claim 13 that includes a transceiver associated with the tracking device that is in two-way communication with the surgical navigation system.

26. The system of claim 25, wherein the transceiver is integrally formed with the tracking devices.

27. A system for determining a position of a skeletal structure, comprising:
   a surgical navigation system having a display;
   a tracking device having a rigid section configured for insertion into a subject, the section including a first end and a second end, the section further having a small cross section relative to a length of the section;
   a joint having first and second degrees of freedom connected to the first end of the section;
   a tip attached to the joint, wherein the tip comprises means for being removably attached to the skeletal structure;
   at least three position-indicating sensors on the second end of the section in a fixed relation to each other, wherein the position-indicating sensors can be tracked by the surgical navigation system;
   a fourth sensor associated with the joint configured to provide the surgical navigation system with a relative position of the tip relative to the position-indicating sensors;
   a first circuit configured for calculating a global position of the skeletal structure by correlating global positional information from the position-indicating sensors and relative position information from the fourth sensor; and
   a second circuit for displaying the global position of the anatomical structure on the display.

28. The system of claim 27 that includes a body at the second end of the section and the three position-indicating sensors are located on the body.

29. The system of claim 28, wherein the body is integral with the section.

30. The system of claim 28, wherein the body is perpendicular to an axis of the section.

31. The system of claim 27, wherein the joint has two degrees of freedom defined by a rotating joint and a pivot joint, and the joint is configured for rotation in all directions.

32. The system of claim 27, wherein the position-indicating sensors are located at a known fixed distance from the joint.

33. The system of claim 27, wherein the position-indicating sensors are located co-linear with the axis of the section.

34. The system of claim 27, wherein the position-indicating sensors comprise an optical tracking element.

35. The system of claim 34, wherein the optical tracking element includes a LED.

36. The system of claim 27, wherein the apparatus includes an internal battery.

37. The system of claim 27, wherein the apparatus includes a transceiver associated with the tracking device that is configured for two-way communication with the surgical navigation system.

38. The system of claim 37, wherein the transceiver is integrally formed with the tracking device.

39. The system of claim 27, wherein an external power supply provides energy to the tracking device through a wire.

40. A system for determining a position of an anatomical structure, comprising:
   a surgical navigation system having a display;
   a tracking device comprising:
      a flexible section configured for insertion into a subject, the section including a first end and a second end, the section further having a small cross section relative to a length of the section;
      a tip disposed on the first end of the section, wherein the tip comprises means for being removably attached to a skeletal structure;
      three position-indicating sensors disposed on the second end of the section, wherein the sensors can be tracked by the surgical navigation system;
      a fourth sensor associated with the flexible section to provide the surgical navigation system with a relative position of the tip relative to the three position-indicating sensors; and
      a transceiver associated with the tracking device configured for two-way communication with the surgical navigation system;

a first circuit configured for calculating a global position of the skeletal structure by correlating global positional information from the tracking device and relative positional information from the sensor; and a second circuit configured for displaying the global position of the anatomical structure on the display.

41. The system of claim 40 that includes a body at the second end of the section and the three position-indicating sensors are located on the body.

42. The system of claim 41, wherein the body is integral with the section.

43. The system of claim 41, wherein the body is perpendicular to an axis of the section.

44. The system of claim 40, wherein the position-indicating sensors are located co-linear with the axis of the section.

45. The system of claim 40, wherein the position-indicating sensors comprise an optical tracking element.

46. The system of claim 45, wherein the optical tracking element includes a LED.

47. The system of claim 40, wherein the transceiver is integrally formed with the tracking device.

48. The system of claim 40, wherein an external power supply provides energy to the tracking device through a wire.

49. The system of claim 40, wherein the apparatus includes an internal battery.

50. A system for determining a position of an anatomical structure, comprising:
   a surgical navigation system having a display;
   a minimum of two tracking devices, wherein at least one of the two tracking devices comprises:
      a rigid section configured for insertion into a body, the section including a first end and a second end, the section further having a small cross section relative to a length of the section,
      a tip on the first end of the section, wherein the tip comprises means for being removably attached to the anatomical structure,
      a transceiver associated with the tracking device that is in two-way communication with the surgical navigation system, and
      a position-indicating sensor on the second end of the section, wherein the position-indicating sensor can be tracked by the surgical navigation system;
   a first circuit for calculating a global position of the anatomical structure by correlating positional information from the two tracking devices; and
   a second circuit for displaying the global position of the anatomical structure on the display.

51. The system of claim 50 that includes a body at the second end of the section and the position-indicating sensor is located on the body.

52. The system of claim 51, wherein the body is integral with the section.

53. The system of claim 51, wherein the body is perpendicular to an axis of the section.

54. The system of claim 50, wherein the position-indicating sensor is located co-linear with the axis of the section.

55. The system of claim 50, wherein the position-indicating sensor comprises an optical tracking element.

56. The system of claim 55, wherein the optical tracking element includes a LED.

57. The system of claim 50, wherein the transceiver is integrally formed with the at least one of the two tracking devices.

58. The system of claim 50, wherein an external power supply provides energy to the tracking device through a wire.

59. The system of claim 50, wherein the apparatus includes an internal battery.

\* \* \* \* \*